United States Patent [19]
Dietz

[11] 3,975,203
[45] *Aug. 17, 1976

[54] COMPOSITION FOR USE AS A FILLER IN TOOTH FILLING AND FACING COMPOSITION AND METHOD OF MAKING THE SAME

[75] Inventor: Earl D. Dietz, Toledo, Ohio

[73] Assignee: Owens-Illinois, Inc., Toledo, Ohio

[ * ] Notice: The portion of the term of this patent subsequent to Apr. 2, 1991, has been disclaimed.

[22] Filed: Feb. 20, 1974

[21] Appl. No.: 444,062

Related U.S. Application Data

[60] Continuation of Ser. No. 158,547, June 30, 1971, Pat. No. 3,801,344, which is a division of Ser. No. 12,109, Feb. 17, 1970, abandoned.

[52] U.S. Cl. ................................ 106/299; 106/35; 106/39.6; 106/288 B; 106/300; 106/303; 106/306; 32/15
[51] Int. Cl.² .................... A61K 5/01; C08K 3/22; C08K 3/40
[58] Field of Search ............ 106/35, 300, 306, 39.6, 106/288 B; 260/42; 32/15

[56] References Cited
UNITED STATES PATENTS

| | | | |
|---|---|---|---|
| 2,826,778 | 7/1974 | Dietz | 260/42.47 |
| 3,305,371 | 2/1967 | de Lajorte | 106/52 |
| 3,467,534 | 9/1969 | MacDowell | 106/52 |
| 3,503,128 | 3/1970 | Boyd | 106/35 |
| 3,504,437 | 8/1970 | Siegel | 106/35 |
| 3,541,688 | 11/1970 | McLean et al. | 32/8 |
| 3,578,470 | 5/1971 | Bahat et al. | 106/39 |
| 3,801,344 | 4/1974 | Dietz | 106/300 |

OTHER PUBLICATIONS

Thomas, Journal of the American Ceramic Society, vol. 33, pp. 35–44.

*Primary Examiner*—Allan Lieberman
*Attorney, Agent, or Firm*—Richard D. Heberling; E. J. Holler

[57] ABSTRACT

A filler composition for tooth filling and facing compositions comprising (1) a finely divided inorganic material, and (2) a barium aluminosilicate glass or other glass having an effective amount of radiopaque oxide that renders the resultant glass radiopaque to X-rays used by dentists. The filler composition is mixed with an organic polymer such as methyl methacrylate to provide a tooth filling and facing composition having an outstanding combination of desirable properties including a color resembling that of natural teeth, a suitable index of refraction, hardness, wear resistant, a relatively low thermal expansion matching that of natural teeth, and being radiopaque to X-rays used by dentists.

21 Claims, 1 Drawing Figure

BaO - Al₂O₃ - SiO₂ GLASSES
LINEAR ABSORPTION COEFFICIENTS
Vs COMPOSITION (WEIGHT PER CENT)

LARGE CIRCLE "I"
GLASS FORMING REGION
AT ABOUT 3000°F

DASHED CIRCLE "II"
BEST COMBINATION OF
GLASS FORMATION AND
HIGH LINEAR
ABSORPTION COEFFICIENT

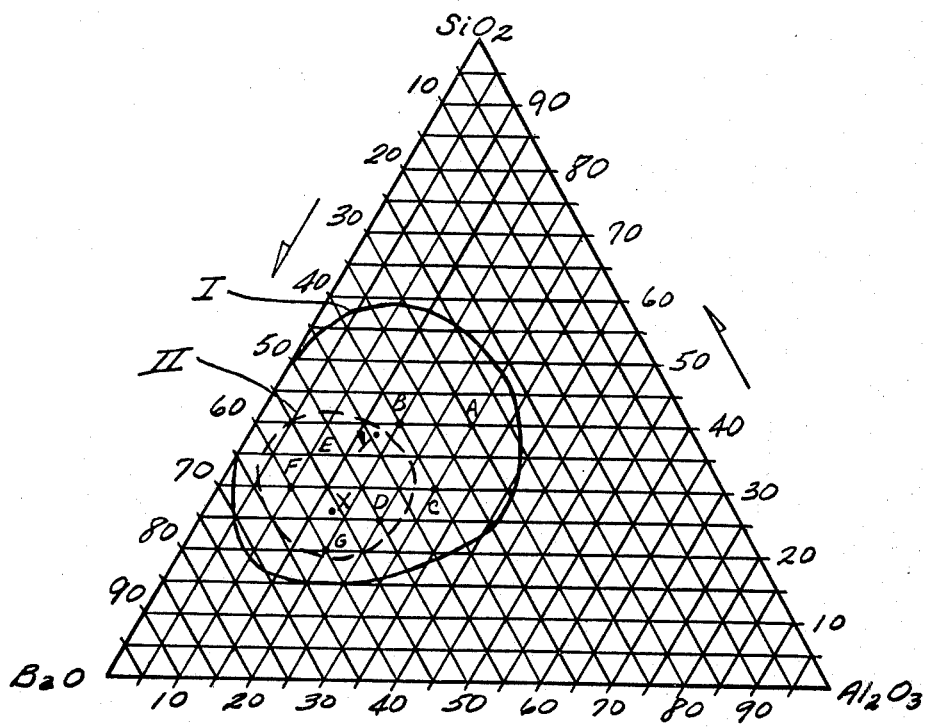

COMPOSITION FOR USE AS A FILLER IN TOOTH FILLING AND FACING COMPOSITION AND METHOD OF MAKING THE SAME

The present application is a continuation of copending application Ser. No. 158,547 filed Jun. 30, 1971, now U.S. Pat. No. 3,801,344, which in turn is a divisional application of copending application Ser. No. 12,109 filed Feb. 17, 1970, now abandoned.

THE INVENTION

The present invention relates to a tooth filling and facing material having a combination of desirable properties including color resembling that of natural teeth, a compatible index of refraction, strength, hardness, a thermal coefficient of expansion matching that of natural teeth, and being radiopaque to X-rays used by dentists. The invention particularly relates to a tooth filling and facing composition having a mixture of finely divided inorganic material and a radiopaque glass as a filler and an organic polymer as a binder.

In the past, there has been a problem in providing a suitable tooth filling and facing composition containing a filler composition and an organic polymer such as polymethyl methacrylate. The tooth filling and facing composition must have a combination of properties that includes a low coefficient of thermal expansion to match that of natural teeth, strength, hardness, wear resistance, a color resembling that of natural teeth, and a compatible index of refraction while providing enough X-ray absorption to allow detection of the filled tooth. It has been difficult to provide a composition having all of the above-described properties, particularly one that has a thermal coefficient of expansion to match that of natural teeth and still is radiopaque to X-rays used by dentists.

It is an object of the present invention to provide a composition for use as a filler in tooth filling and facing compositions in which the filler composition comprises (1) a finely divided inorganic material and (2) a glass having an effective amount of a radiopaque producing oxide that renders the resultant glass radiopaque to X-rays used by dentists, the filler composition being capable of producing an outstanding tooth facing and filling material when mixed with an organic polymer, the resultant tooth repairing material having a combination of properties including a color resembling that of natural teeth, a suitable index of refraction, hardness, strength, wear resistance, a relatively low thermal expansion matching that of natural teeth, and being radiopaque to X-rays.

It is an object of the present invention to provide a filler composition for a tooth filling and facing composition and a method of making the filler composition and the tooth filling and facing composition.

These and other objects will be apparent from the specification that follows, the appended claims and the drawings in which:

The FIGURE is a ternary compositional diagram of BaO-Al$_2$O$_3$-SiO$_2$ glass systems showing suitable and preferred glasses that are radiopaque to X-rays used by dentists and are adapted for use as fillers in tooth filling and facing compositions.

The present invention provides a filler composition for use as a filler and tooth facing and filling composition comprising a finely divided inorganic material and a glass having an effective amount of a radiopaque-producing oxide that renders the resultant glass radiopaque to X-rays used by dentists. The resultant filler composition is incorporated in an organic binder such as an acrylic resin that produces a filling and facing composition that has a color resembling that of natural teeth, has a suitable index of refraction, has desired hardness and wear resistance, has relatively low thermal expansion matching that of natural teeth, and is radiopaque to X-rays used by dentists.

It is preferred that the radiopaque glass filler be a barium aluminosilicate glass with a BaO content greater than about 22.5 percent by weight, such glass rendering the tooth filling and facing composition radiopaque to X-rays used by dentists. Furthermore, the resultant tooth filling and facing composition containing the barium aluminosilicate glass has a desirable color like that of natural teeth, a suitable index of refraction, high strength, wear resistance, a low thermal expansion matching that of natural teeth, and is non-toxic. Generally, the barium aluminosilicate glass is one consisting of BaO, Al$_2$O$_3$ and SiO$_2$ in the relative proportions by weight shown within the area marked by line I of the ternary diagram shown in the FIGURE. It is highly preferred that the radiopaque glass be one consisting essentially of BaO, Al$_2$O$_3$ and SiO$_2$ in the relative proportions by weight shown inside the area marked by line II in the ternary diagram shown in the FIGURE. The optimum radiopaque glass is one consisting essentially of about 25–35 parts by weight of SiO$_2$, 10–20 parts by weight of Al$_2$O$_3$, and 50–60 parts by weight of BaO.

As previously indicated, a part of the filler composition is a finely divided inorganic material such as glass-ceramic material, quartz, fused silica, calcite, calcium carbonate, wollastonite, or other hard, finely divided inorganic filler having generally a mesh size of about 20 to 400 mesh, and preferably about 100 to 200 mesh.

The filler composition which is inorganic material and the radiopaque glass is used in amounts of about 20–80 parts by weight with about 20–80 parts by weight of an organic polymer binder. The organic polymer is preferably an acrylic resin such as polyethyl methacrylate, polyethyl acrylate and polymethyl methacrylate and it is highly preferred that the resin be polymethyl methacrylate.

The acrylic polymer can be prepared from a monomer or mixtures of monomers having the general formula

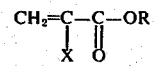

where R is an alkyl group of 1 to 3 carbon atoms and X is H or an alkyl group of 1 to 2 carbon atoms. The above acrylic monomers can be used in an amount of about 100 parts by weight with about 2 to 30 parts by weight of another copolymerizable monomer such as styrene, butadiene, ethylene and acrylic acid to provide a suitable polymer for the tooth repairing conpositions. Other polymers can be used such as polyvinyl chloride, cellulose acetate, and styrene acrylonitrile copolymer providing the resultant composition is radiopaque, has the desired color, index of refraction, strength, wear resistance, thermal expansion and is non-toxic. The filler composition itself generally comprises about 50–90 parts by weight of the glass-ceramic material or other inorganic filler and about 10–50 parts by weight of radiopaque glass. Preferred amounts of the inorganic filler preferably having a low thermal coefficient of expansion are about 60–80 parts by weight to about 20–40 parts by weight of the preferred barium aluminosilicate glass or other radiopaque glass. The optimum amounts are about 70–75 parts by weight of the inorganic material and about 25–30 parts by weight of the glass. A highly preferred filler composition is one having about 70 parts by weight of a glass-ceramic consisting essentially of $SiO_2$, $Li_2O$, $Na_2O$, $K_2O$, $CaO$, $Sb_2O_3$, $Al_2O_3$, $ZrO_2$ and $TiO_2$ with about 30 parts by weight of a radiopaque glass having the following ingredients in approximate percent by weight:

| INGREDIENTS | PERCENT |
|---|---|
| $SiO_2$ | 25–35 |
| $Al_2O_3$ | 10–20 |
| $BaO$ | 50–60 |

An especially useful glass-ceramic for obtaining the best balance of desired properties contains the following ingredients in approximate percent by weight:

| INGREDIENTS | PERCENT |
|---|---|
| $SiO_2$ | 67 |
| $Al_2O_3$ | 20 |
| $TiO_2$ | 1.7 |
| $ZrO_2$ | 2 |
| $Sb_2O_3$ | .3 |
| $CaO$ | 3.5 |
| $Li_2O$ | 4 |
| $Na_2O$ | 0.4 |
| $K_2O$ | 0.2 |

An especially useful radiopaque glass is one that contains the following ingredients in approximate percent by weight:

| INGREDIENTS | PERCENT |
|---|---|
| $SiO_2$ | 26 |
| $Al_2O_3$ | 18 |
| $BaO$ | 56 |

Although the preferred radiopaque-producing oxide by far is barium oxide, it giving the best color and all around properties to the resultant composition, other radiopaque-producing oxides such as strontium can be used. Also suitable but not as good as strontium oxide are lanthanum and other rare earth oxides of the lanthanide series, Nos. 57–71 such as samarium oxide, dyprosium oxide and terbium oxide can be used in which the mass absorption coefficient of the element (including scattering) is generally above about 300 and preferably above about 350 for $Cuk\alpha$, 1.5418 A. The mass absorption coefficient of Ba is given as 359 and lanthanum as 378. However, the lanthanum oxide generally imparts some undesirable color to the tooth filling and facing composition as does praseodymium oxide.

The following example illustrates the present invention.

EXAMPLE

A series of filler compositions comprising 30 parts by weight of barium aluminosilicate glass mixed with 70 parts by weight of a glass-ceramic were prepared and the resultant filler compositions mixed in an amount of about 40 parts by weight with 50 parts by weight of a liquid, solvent-soluble, further curable, methyl methacrylate polymer. The glass-ceramic used was one containing the following ingredients in approximate percent by weight:

| INGREDIENTS | PERCENT |
|---|---|
| $SiO_2$ | 67 |
| $Al_2O_3$ | 20 |
| $TiO_2$ | 1.7 |
| $ZrO_2$ | 2 |
| $Sb_2O_3$ | .3 |
| $CaO$ | 3.5 |
| $Li_2O$ | 4 |
| $Na_2O$ | 0.4 |
| $K_2O$ | 0.2 |

The barium aluminosilicate glass used was one of the following series in which the ingredients are given in weight percent and mole percent.

| | Weight Percent | | | Mole Percent | | |
|---|---|---|---|---|---|---|
| | $SiO_2$ | $Al_2O_3$ | $BaO$ | $SiO_2$ | $Al_2O_3$ | $BaO$ |
| A | 40 | 30 | 30 | 58 | 25 | 17 |
| B | 40 | 20 | 40 | 59 | 18 | 23 |
| C | 30 | 30 | 40 | 48 | 28 | 25 |
| D | 25 | 25 | 50 | 42 | 25 | 33 |
| E | 40 | 10 | 50 | 61 | 9 | 30 |
| F | 30 | 10 | 60 | 51 | 10 | 39 |
| G | 20 | 20 | 60 | 36 | 22 | 42 |
| X | 26 | 18 | 56 | 44 | 18 | 38 |
| Y | 38.2 | 15.5 | 46 | 59 | 14 | 28 |

The resultant mixture was used as a tooth facing and filling composition, the mixture being formed to the desired shape and the organic binder being cured by heating or at room temperature to thereby remove the solvent and form a thermoset polymer that binds the finely divided filler within its matrix.

The resultant compositions all had an outstanding combination of properties including a color resembling that of natural teeth, strength, wear resistance, abrasion resistance, a low thermal expansion matching that of natural teeth and were radiopaque to X-rays used by dentists. The mass absorption coefficients were calculated for copper $K\alpha$ radiation which has a wavelength of about 1.5418 A. From the standpoint of glass processing including a desirable liquidus, compatible index of refraction and absorption coefficient, it is highly preferred that the radiopaque barium aluminosilicate glasses be ones having compositions similar to that of F and G in the above Table. Hence, the optimum glasses contain about 18–32 weight percent $SiO_2$, 8–22 weight percent $Al_2O_3$ and about 56–62 weight percent $BaO$. Glasses in the barium aluminosilicate system shown in the area bounded by line I of the FIGURE are advantageous because they have low coefficients of thermal expansion in the range of about 55–60 up to 70 or 75 × $10^{-7}$/°C. and have an index of refraction similar to that of natural teeth. The calculated X-ray absorption coefficients of the barium aluminum silicate glasses shown in A through G, X and Y in the Table are as follows:

| | Mass Absorption Coefficient | Density | Linear Absorption Coefficient |
|---|---|---|---|
| A | 83.5 | 2.7 | 223 |
| B | 101 | 2.9 | 293 |
| C | 106.9 | 3.2 | 342 |
| D | 129.8 | 3.5 | 454 |
| E | 121.5 | 3.2 | 388 |

-continued

| | Mass Absorption Coefficient | Density | Linear Absorption Coefficient |
|---|---|---|---|
| F | 148 | 3.7 | 548 |
| G | 156.3 | 4.0 | 626 |
| X | 144.8 | 3.7 | 536 |
| Y | 115.8 | 3.0 | 348 |

The mass absorption coefficients for the elements for CuKα, 1.5418 A, were taken from Appendix V, X-RAY DIFFRACTION PROCEDURES, H. P. Klug and L. E. Alexander, John Wiley & Sons, New York 1959.

As seen in the above Table, generally the linear absorption coefficient can be as low as about 200 to 220 although it is preferred that the coefficient be at least about 340 or 350.

As can be noted in an article by R. H. Thomas entitled "Equilibrium In A Portion Of The Ternary System $BaO-Al_2O_3-SiO_2$", JOURNAL AMERICAN CERAMIC SOCIETY, Vol. 33, February 1950, pages 35–44, the liquidus temperatures of the glasses inside the area of line I are within the range of about 1300° to 1700°C. and hence are easily melted, processed and formed. The preferred compositions have a liquidus in the range of about 1400° to 1600°C.

What is claimed is:

1. A composition for use as a filler in tooth filling and facing compositions comprising 50–90 parts by weight of a finely divided inorganic material and 10–50 parts by weight of a barium aluminosilicate glass having a BaO content than about 22.5 percent by weight, the facing and filling composition being radiopaque to X-rays used by dentists, having a color like that of natural teeth, an index of refraction like that of natural teeth, high strength and wear resistance, and a low coefficient of thermal expansion matching that of natural teeth and being non-toxic.

2. The invention of claim 1 wherein said barium alumino-silicate glass consists essentially of BaO, $Al_2O_3$ and $SiO_2$ in the relative proportions by weight shown inside the area of line I in the ternary diagram of the FIGURE.

3. The invention of claim 2 wherein said barium alumino-silicate glass consists essentially of BaO, $Al_2O_3$ and $SiO_2$ in the relative proportions by weight shown inside the area of line II in the ternary diagram of the FIGURE.

4. The invention of claim 1 wherein the barium alumino-silicate glass consists essentially of about 18 to 32 percent by weight $SiO_2$, about 8 to 22 percent by weight $Al_2O_3$ and 56 to 62 percent by weight BaO.

5. The invention of claim 1 wherein the barium aluminosilicate glass consists essentially of about 25 to 35 percent by weight $SiO_2$, about 10 to 20 percent by weight $Al_2O_3$ and about 50 to 60 percent by weight BaO.

6. The invention of claim 1 wherein said inorganic material is selected from the group consisting of glass-ceramic material, quartz, fused silica, calcite, $CaCO_3$ and wollastonite, having a low coefficient of thermal expansion.

7. The invention of claim 6 wherein said glass-ceramic material consists essentially of $SiO_2$, $Li_2O$, $Na_2O$, $K_2O$, CaO, $Sb_2O_3$, $Al_2O_3$, $ZrO_2$ and $TiO_2$.

8. The invention of claim 1 wherein said inorganic material constitutes 60 – 80 parts by weight and said barium aluminosilicate glass constitutes 20 – 40 parts by weight, said parts by weight being based upon the combined weight of said inorganic material and barium aluminosilicate glass.

9. The invention of claim 8 wherein said inorganic material constitutes 70 – 75 parts by weight and said barium aluminosilicate glass constitutes 25 – 30 parts by weight, said parts by weight being based upon the combined weight of said inorganic material and barium aluminosilicate glass.

10. The invention of claim 1 wherein the particle size of said finely divided inorganic material is between about 20 and 400 mesh.

11. The invention of claim 10 wherein the particle size of said finely divided inorganic material is between about 100 and 200 mesh.

12. The invention of claim 1 wherein said barium alumino-silicate glass has an X-ray linear absorption coefficient of at least 200.

13. The invention of claim 12 wherein said barium alumino-silicate glass has an X-ray linear absorption coefficient between 223 and 626.

14. The invention of claim 1 wherein said barium alumino-silicate glass has a coefficient of thermal expansion in the range of about $55 \times 10^{-7}$/°C to about $75 \times 10^{-7}$/°C.

15. A method for making a composition for use as a filler in tooth facing and filling compositions having an outstanding balance of properties including being radiopaque to X-rays used by dentists, having a color like that of natural teeth, a index of refraction like that of natural teeth, high strength and wear resistance, and a low coefficient of thermal expansion matching that of natural teeth and being non-toxic, the method comprising the step of mixing together 50–90 parts by weight of a finely divided inorganic material and 10–50 parts by weight of a barium aluminosilicate glass containing a BaO content greater than about 22.5 percent by weight so that the resultant glass is radiopaque to X-rays used by dentists.

16. The invention of claim 15 wherein said barium alumino-silicate glass consists essentially of BaO, $Al_2O_3$ and $SiO_2$ in the relative proportions by weight shown inside the area of line I in the ternary diagram of the FIGURE.

17. The invention of claim 16 wherein said barium alumino-silicate glass consists essentially of BaO, $Al_2O_3$ and $SiO_2$ in the relative proportions by weight shown inside the area of line II in the ternary diagram of the FIGURE.

18. The invention of claim 15 wherein said inorganic material is selected from the group consisting of glass-cermaic material, quartz, fused silica, calcite, $CaCO_3$ and wollastonite, having a low coefficient of thermal expansion.

19. The invention of claim 15 wherein the particle size of said finely divided inorganic material is between about 20 and 400 mesh.

20. The invention of claim 15 wherein said barium alumino-silicate glass has an X-ray linear absorption coefficient of at least 200.

21. The invention of claim 15 wherein said barium aluminosilicate glass has a coefficient of thermal expansion in the range of about $55 \times 10^{-7}$/°C to about $75 \times 10^{-7}/20$ C.

* * * * *